United States Patent [19]

Döring et al.

[11] Patent Number: 5,510,268
[45] Date of Patent: Apr. 23, 1996

[54] METHOD AND DEVICE FOR DETECTING SUBSTANCES IN AN AMBIENT SUBSTANCE, IN PARTICULAR FOR DETECTING CHEMICAL WARFARE AGENTS

[76] Inventors: Hans-Rüdiger Döring, Ludwigstrasse 13, D-7050 Leipzig; Eberhard Hartmann, Stuttgarter Allee 18, D-7060 Leipzig, both of Germany

[21] Appl. No.: 308,947

[22] Filed: Sep. 20, 1994

Related U.S. Application Data

[63] Continuation of Ser. No. 955,869, filed as PCT/DE91/00295, Apr. 9, 1991, abandoned.

[51] Int. Cl.$^6$ .................................................. G01N 27/66
[52] U.S. Cl. ...................... 436/103; 436/104; 422/82.01
[58] Field of Search .......................... 436/103, 104–105; 422/82.01

[56] References Cited

PUBLICATIONS

Article "Detection of Chemical Warfare Agents by Means of an Ionization Chamber Operated in AC Mode" by S. Milinkovic et al. in "Proc. 3rd Int. Symp. Protection Against Chemical Warfare Agents" in Umea, Sweden, Jun. 11–16, 1989.
Periodical "Isotopenpraxis," vol. 26, No. 4, pp. 176–180 (1990), "The Self–Consistent Charge Method: A Numerical Approach to Radiation–Induced Charge Transport Phenomena" by E. Hartmann et al.
Article "New Ion Mobility Techniques" by C. Blanchard, in "Proceedings of the 1987 U.S. Army Scientific Conference on Chemical Defense Research" Aberdeen Proving Ground, MD, CRDBC–Sp–88013, 1971 (Apr. 1988).

*Primary Examiner*—Lyle A. Alexander
*Attorney, Agent, or Firm*—Claude A. S. Hamrick

[57] ABSTRACT

The invention relates to a method and an apparatus for individually detecting in ambient air a predetermined gaseous warfare agent, namely a poison gas of the class of organic sulfuric or phosphorous substances, and a predetermined interfering compound, e.g. another poison gas. First, light $O_2$ reaction ions are generated from water and are added in a measuring chamber to a mixture of the agent and the ambient air. As a result, the $O_2$ reaction ions will deposit on the heavy molecules of the agent in a spatially non-uniform distribution to generate quasi-molecular ions. An electrical field alternating about a zero line and having a predetermined basic frequency and an amplitude is generated within the measuring chamber. The resulting quasi-molecular ion current is measured and resulting current signals are processed. For distinguishing the agent from the interfering compound, an initial experiment is made for a standardized measuring chamber. During the initial experiment, the quasi-molecular current is determined as a function of the basic frequency, of the amplitude and of a plurality of asymmetries of the electrical field variation relative to the zero line. Each current determination is carried out separately for the agent and for the interfering compound. Then a first measurement on the mixture of ambient air, agent and interfering compound is made with a first one of the asymmetries and, subsequently, a second measurement on the mixture is made with a second one of the asymmetries. The measured signals of these two measurements are logically combined to extract an output signal indicative of the presence of the agent and of the interfering compound within the ambient air.

22 Claims, 3 Drawing Sheets

METHOD AND DEVICE FOR DETECTING SUBSTANCES IN AN AMBIENT SUBSTANCE, IN PARTICULAR FOR DETECTING CHEMICAL WARFARE AGENTS

This is a continuation of application(s) Ser. No. 07/955,869 filed as PCT/DE91/00295, Apr. 9, 1991 now abandoned.

BACKGROUND OF THE INVENTION

Description of the Related Art

The invention concerns a process for detecting measured substances in an ambient substance, especially for detecting gaseous warfare agents in ambient air, in which light reaction ions are first generated from a reaction substance and are added to the mixture of measured substance and ambient substance, in such a way that reaction ions in a spatially inhomogeneous distribution in a measurement chamber attach themselves to heavy molecules of the measured substance to form molecular ions; and that in the measurement chamber, an electric field that varies over time, alternates about a zero line, and has a predefined basic frequency and amplitude, is generated, the molecular ion current resulting from the electric field is measured, and the measured signal is analyzed.

The invention further concerns a device for detecting measured substances in an ambient substance, especially for detecting gaseous warfare agents in ambient air, with a measurement chamber, with first means for introducing the mixture of measured substance and ambient substance into the measurement chamber; with second means for generating light reaction ions from a reaction substance and for adding the reaction ions to the mixture; with third means for attaching the reaction ions to heavy molecules of the measured substance in the measurement chamber; with fourth means for generating in the measurement chamber an electric field which alternates a bout a zero line and has a predefined basic frequency and amplitude, with the fourth means being configured as an electrode pair in the measurement chamber and as a voltage source connected to the electrode pair; and with fifth means for detecting and analyzing the molecular ion current caused by the electric field in the chamber.

The closest known prior art device is disclosed in the article entitled "Detection of Chemical Warfare Agents by Means of an Ionization Chamber Operated in AC Mode," by S. Milinkovic et al., in "Proc. 3rd Int. Symp. Protection Against Chemical Warfare Agents", Umea, Sweden, Jun. 11–16, 1989.

In many areas of environmental protection and military engineering, it is desirable to be able to detect certain measured substances, preferably hazardous measured substances, in an environment consisting of air, water, or the like. If extremely dangerous measured substances, for example gaseous warfare agents, are to be detected in this context, not only are high detection sensitivity and reliability desirable, but stringent demands are also made in terms of response speed. This is especially true when it is not known if the measured substances in question are present in the relevant environment at all, since constant monitoring for the occurrence of these measured substances then takes place, and an alarm must be triggered as quickly as possible if the occurrence of these measured substances is observed.

In the area of military engineering, this applies especially to the area of toxic gases, which are known in a variety of compositions and effects.

For example, toxic gases are essentially differentiated into vesicants on the one hand, and nerve poisons on the other. While vesicants act on the human skin, where they cause erosion and burning, nerve poisons act on the human nervous system, leading to respiratory paralysis and the like.

The best known of the vesicants are the mustard gases, in this case especially the 2,2'-dichlorodiethyl sulfide known as sulfur mustard, with the structural formula:

Cl—CH$_2$—CH$_2$—S—CH$_2$—CH$_2$—Cl and the tris(2-chloroethyl) amine with the structural formula:

or

CH$_3$
|
Cl—CH$_2$—CH$_2$—N—CH$_2$—CH$_2$—Cl

Among the nerve poisons, the most important are the dimethylphosphoramidocyanidic acid ethyl ester known as Tabun, with a molecular weight of 162 amu and the following structural formula:

(CH$_3$)$_2$N—P—CN
|
O—C$_2$H$_5$ and the O-isopropyl or -pinacolyl ester of methylphosphonofluoridic acid known as Sarin or Soman, with molecular weights between 140 and 182 amU and the following structural formula:

R—C—O—P—F    R = —CH$_3$    R = —C(CH$_3$)$_3$

Last to be mentioned of the gaseous warfare agents are the phosphorylthiocholines known generally as V agents, with molecular weights of 267 amU and the following structural formula:

RO—P—SCH$_2$CH$_2$NR$_2$
|
R especially "VX", with an even higher molecular weight and the following structural formula:

C$_2$H$_5$—O—P—SCH$_2$CH$_2$N(iC$_3$H$_7$)$_2$
|
CH$_3$

A variety of processes and devices for detecting these chemical warfare agents are already known. Some of these known processes and devices are based on the detection of mobile ions.

For example, the article by Milinkovic mentioned earlier describes a coaxial ionization chamber in which, in a cylindrical housing, a radial inlet tube and a radial outlet tube opposite it are provided for a gas mixture. For this purpose, gas is drawn in from the environment and sucked in through the inlet tube into the measurement chamber, being then discharged from it through the outlet tube once the measurement has been made.

The known measurement chamber uses a cylindrical electrode arrangement with an axial inner electrode and an outer electrode arranged on the cylindrical enveloping surface, with the gas flow under investigation flowing through the gap between the two electrodes. A radiation source that also influences the volume through which the gas flows is located at the axial end of the measurement chamber in a radial plane.

In the known device, ambient air is then pumped through the measurement chamber at a constant flow rate, and ionized by the radioactive source. The result of this is to form "reaction ions" from the ambient air ($O_2$, $N_2$) in combination with atmospheric moisture ($H_2O$). Specifically, this occurs as follows:

First the ambient air ($O_2$, $N_2$) is ionized under the action of β radiation, forming $O_2+$ and $N_2+$ ions and free electrons $e^-$.

If we now consider the $N_2+$ ions, for example, these first bind to a nitrogen molecule $2N_2$ to form $N_4+$ and $N_2$. The $N_4+$ in turn reacts with atmospheric moisture ($H_2O$) to form $2N_2$ and $H_2O^+$. The $H_2O^+$ in turn reacts with the $H_2O$ in the atmospheric moisture to form $H_3O^+$ and OH, which corresponds to a reaction between $(H_2O)H^+$ and $H_2O$ to form the positive reaction ions $(H_2O)_8H^+$. This positive reaction ion has a weight of 145 amU and a mobility of 2 cm$^2$/Vs.

Similarly, it can be shown for the negative reaction ions that the $O_2$ and the free electrons $e^-$ ultimately react with atmospheric $H_2O$ to form $(H_2O)_6O_2$, the negative reaction ion. This has a weight of about 140 amU and a mobility also on the order of 2 cm$^2$/Vs.

The positive and negative reaction ions explained above now react with the molecules of any gaseous warfare agents that may be present. If the molecules of the nerve poisons (organophosphorus compounds) are referred to as $M_A$ and the molecules of the vesicants, especially sulfur mustard, as $M_B$, the following reactions can then be written:

$(H_2O)_8H^+ + M_A \rightarrow M_A(H_2O)_6H^+ + 2H_2O$ $M_A(H_2O)_6H^+ + M_A \rightarrow M_{A2}H^+ + 6H_2O$ with the the formation of $M_{A3}H^+$ also possible at higher concentrations of organophosphorus compounds.

With the vesicants, the corresponding reaction is as follows:

$(H_2O)_6O_2^- + M_B \rightarrow M_B(H_2O)_4O_2^- + 2H_2O$

The quasi-molecular ions or product ions formed in this manner have, in the case of the organophosphorus compounds, a mobility on the order of 1.5 to 0.5 cm$^2$/Vs at a molecular weight in the range between 250 and 700 amu, while for the vesicants (sulfur mustard), the ion mobility is approximately 1.5 cm$^2$/Vs with a molecular weight of 250 amu.

The above explanation shows the expected result, namely that the reaction ions are considerably lighter in weight and faster in terms of mobility than the product ions or quasi-molecular ions, with considerably higher molecular weights along with lower mobility.

For the sake of simplicity, the abbreviations "$H^+$" and "$O_2^-$" for the reaction ions, and the abbreviations "$M_A+$" and "$M_B-$" for the quasi-molecular ions, will be used in the description which follows.

If the gas flowing through the measurement chamber now also contains measured substances, especially gaseous warfare agents, that have molecules with a considerably higher molecular weight, the aforementioned reaction ions will then attach themselves to the molecules of the measured substances.

The type of attachment—i.e. whether the positively charged protons or the negatively charged oxygen ions attach to the molecules of the measured substances—depends on the nature of the measured substances.

In the case of the gaseous warfare agents explained above, conditions are such that with the mustard gases, the negatively charged reaction ions attach to the mustard molecules, while with the nerve poisons (Tabun, Sarin, Soman, V agents, and especially VX), a proton transfer occurs from the positively charged reaction ions to the warfare agent molecules. In the case of the latter reaction, it is also possible that in each case two molecules of the measured substance will bind a proton in pairs.

It is especially important in the present connection that with both types of gaseous warfare agents, namely with the vesicants (mustards) on the one hand and the nerve poisons (Tabun, Sarin, Soman, VX agents) on the other, differently charged molecular ions, namely negatively charged quasi-molecular ions for the vesicants and positively charged quasi-molecular ions for the nerve poisons, are formed in the respective cases.

It is also important, in the case of the known device, that the radioactive source is arranged so that it produces a spatially inhomogeneous distribution of reaction ions and thus also of quasi-molecular ions in the measurement volume of the measurement chamber. The inhomogeneity of the spatial distribution is configured so that on average, the distance from the quasi-molecular ions to one electrode is greater than the distance to the other electrode.

In the known device, an alternating current is then applied to the electrode arrangement. The resulting alternating electric field, i.e. a field oscillating about a zero line, then exerts a force on the quasi-molecular ions in the direction of one electrode during one half-wave, and in the direction of the other electrode during the other half-wave. However, since the average path lengths for the quasi-molecular ions to the two electrodes are, as mentioned, of different lengths, a greater ion current flows during one half-wave than during the other half-wave, since with an electric field of a suitably high frequency, the half-period is not sufficiently long to bring all the relatively heavy quasi-molecular ions to the respective target electrode.

The result, with the known arrangement, is therefore a direct-current component of the ion current. The sign of this direct-current fraction depends on which type of measured substance is present in the ambient air. If it is one of the aforementioned vesicants with negatively charged quasi-molecular ions, the sign of the direct-current component is positive, while with the nerve poisons it is negative.

With the known device, the result is therefore a positive or a negative output signal depending on the type of gaseous warfare agent detected; and it is known that this output signal can be further optimized in terms of amplitude by setting the frequency of the electric field appropriately.

The known device has the disadvantage, however, that it consistently produces measurement errors or even fails if what is present in the environment is not exclusively measured substances of a single type, but rather mixtures of measured substances of both types, for example vesicants and nerve poisons simultaneously.

On the other hand, it is of considerable advantage to be able to have available processes and devices with which, even in situations in which vesicants and nerve poisons are being used simultaneously, both the one and the other substance can be detected quickly and reliably, without having the signals from one substances compensate for the signals of the other substance.

A further problem that arises in the detection of measured substances of the type discussed here is that detection of these measured substances must be differentiated from interfering substances and other interfering factors that occur in a real-world environment.

If we once again consider the area of military engineering in this context, it may for example be necessary in a conflict situation to be able to detect gaseous warfare agents selectively, even when the ambient air is at the same time permeated by hydrocarbon vapors, for example leaking gasoline and diesel fuel, or by smoke or other organic compounds. In addition, detection must also be possible if fluctuations in pressure, temperature, or atmospheric humidity occur during the measurement. The interfering factors just mentioned can occur, for example, if the process is performed on board a vehicle or if the device is located on board a vehicle. If the vehicle is, for example, a helicopter, a measurement device will also be exposed to numerous interfering effects which must suppressed as much as possible when detecting these highly sensitive measured substances.

It is also a known process to use "tandem measurement chambers" to suppress the influence of interfering substances. Such tandem measurement chambers have an unaltered measurement chamber, for example of the type mentioned initially, and also have a second reference chamber in the gas inlet of which is arranged a filter that filters out the substances being measured. When measuring gaseous warfare agents, such a filter can be, for example, the usual filter for a gas mask.

When such a tandem measurement chamber is used in a measurement situation in which, for example, gasoline vapors are acting as an interfering factor, these gasoline vapors are not retained by the reference chamber filter and therefore permeate the measurement chamber and reference chamber simultaneously. Consequently, the readings from the two chambers change simultaneously, so that this type of reading can be eliminated as an interfering variable. On the other hand, if a gaseous warfare agent encounters the tandem measurement chamber, it permeates only the measurement chamber and not the reference chamber, since it is blocked off from the latter by the filter, so that a true reading occurs only in the measurement chamber.

In an alternative configuration, a filter can also be placed in front of a measurement chamber and then removed from it, so that one measurement chamber serves in succession as measurement chamber and reference chamber.

The known arrangements just described have the disadvantage, however, of being encumbered with a long time constant. For example, in reality it is impossible to obtain filters that ideally retain the measured substance and immediately allow free passage of all other substances. In practice, conditions are in fact such that a filter also presents at least some resistance to interfering substances, for example gasoline vapors, with the consequence that the reference chamber is slow to fill up with the interfering substance, while the latter has already penetrated into the measurement chamber without hindrance. To eliminate incorrect measurements, it is therefore always necessary to wait a certain amount of time for equilibrium to occur between measurement chamber and reference chamber. The times required for this in practice are on the order of minutes; but this period is too long for the detection of gaseous warfare agents. What are instead desired are reaction times on the order of, for example, 10 seconds, so that an alarm can be triggered before the suddenly occurring gaseous warfare agents have caused any damage.

The periodical "Isotopenpraxis," Volume 26, No 4, pages 176–180 (1990), discloses a mathematical method for using a Fortran program to find an iterative solution to differential equation systems that are applicable to the kinetics of various physical processes. These include, for example, an ionization gas detector, in which ions present in a measurement chamber are influenced by a pulsed electric field.

The article "New Ion Mobility Techniques" by C. Blanchard, published in "Proceedings of the 1987 U.S. Army Scientific Conference on Chemical Defense Research," Aberdeen Proving Ground, MD, CRDBC-Sp-88013, 1971 (April 1988) discloses an ion mobility spectrometer (IMS) in which non-linear electric fields are applied to the mobile ions. These non-linear electric fields are partly spatially and partly temporally non-linear, and are designed to raise the sensitivity of the spectrometer.

European Patent EP-A-O 253 155 discloses a field-regulating arrangement for an ion mobility spectrometer (IMS) in which a temporally non-linear electric field is also generated. However, the emphasis with this IMS, as with the IMS explained above, is on spatial separation of regions with differing field strength profiles. The possibility of separate detection of two measured substances with differently charged quasi-molecular ions is neither discussed nor possible in this connection.

SUMMARY OF THE INVENTION

The object on which the invention is based is therefore that of developing a process and a device of the aforementioned type in such a way that even with mixtures of different measured substances, especially with mixtures of vesicants and nerve poisons, rapid and differentiated measurement, along with any required alarm, is possible.

According to the invention, this object is achieved, in accordance with a process of the aforementioned type, by the fact that in order to differentiate a first measured substance from a second measured substance present simultaneously in the ambient substance, First, for a defined measurement chamber, the function of the quasi-molecular ion current vs. basic frequency, vs. amplitude, and vs. an asymmetry of the electric field strength vs. time function with respect to the zero line are determined, each time separately for the first and for the second measured substance;

Then a first measurement of the mixture is performed with a first asymmetry;

Then a second measurement of the mixture is performed with a second asymmetry; and The measured signals of the two measurements are logically correlated.

According to the invention, the object is further achieved, in a device of the aforementioned type, by the fact that the voltage source comprises a changeover switch by means of which two voltage profiles with different asymmetries with respect to the zero line can be switched alternatively and successively to the electrode pair; and that the fifth means comprise logical circuit means for comparing the measured values of the quasi-molecular ion current.

The object underlying the invention is completely achieved in this manner.

Specifically, because two measurements are performed in succession with different measurement parameters, it is possible to influence the measured substances in different ways during the two measurements, so that with a suitable measurement chamber, the results are two readings from which the presence of one of the two, or both, measured substances can be determined.

According to this invention, therefore, there is no longer any risk that compensation in readings will occur due to differently polarized quasi-molecular ions.

Moreover, the defined measurement conditions, i.e. the predefined settings for basic frequency, amplitude, and asymmetry, ensure that selectivity is high, thus simultaneously allowing the suppression of interference signals that might result from interfering substances in the environment.

In preferred variants of the process according to the invention, water is used in a known manner as the reaction substance from which the reaction ions are generated by radioactive irradiation. Preferably a B radiator in the measurement chamber is used for this purpose, with its inside dimensions being made considerably greater than the half-life range of the B radiator so as to produce the desired inhomogeneous distribution.

It is moreover preferred if a preferably periodic voltage is used to generate the electric field. It is further preferable if the voltage is given a profile over time having first and second pulses alternating from one to another above and below the zero line.

The first pulses are, in this context, preferably followed immediately in time by the second pulses.

In this connection, a particularly good effect is achieved if the first pulses are made to have the same pulse area as the second pulses.

Preferably the pulses are rectangular in shape, with the first pulses being higher and narrower than the second pulses; also preferably, the first pulses are made to be two to five times as high as the second pulses.

It is especially advantageous if the first and the second asymmetry are produced by the fact that for the first measurement the pulses are given a first polarity, and for the second measurement are given the opposite polarity. This can easily be achieved by simply changing the sign of the voltage.

A basic frequency in the range between 100 and 500 Hz has proved particularly successful for implementing the process according to the invention in the detection of gaseous warfare agents, with the volume of the measurement chamber being set in the range between 0.5 and 5 $cm^3$. The voltage was given an effective value in the range between 50 and 200 V.

In a further group of exemplary embodiments of the process according to the invention, in a further, i.e. third, process step, a constant electric field two to twenty times as strong as the effective value of the alternating electric field is generated in the measurement chamber; the resulting quasi-molecular ion current is measured; and the measured signal obtained thereby is compared with the measured signals of the first and second measurements.

This feature has the advantage that this third comparative measurement sucks up all the free charge carriers in the measurement chamber due to the very high electrical field strength, thus making available a signal that reflects the total number of free charge carriers present in the measurement chamber. Since this total number contributes to the measured signal for both the first and the second measurement, in which neither the concentration of the measured substances nor the concentration of any interfering substances that may be present are, however, known, it is possible to determine these unknown values on the basis of the results of the three measurements.

This procedure has the additional advantage that interfering environmental influences such as fluctuations in pressure, temperature, and humidity are also eliminated, since if the aforesaid three measurements succeed one another immediately in time, these interfering effects contribute equally to all three measurements, and are therefore eliminated from the calculation when calculating the variables of interest, for example the concentration of the measured substance.

In preferred developments of the device according to the invention, the measurement chamber is cylindrical in shape.

This feature has the advantage of resulting in a particularly simple configuration that is both manageable in terms of calculations and results in reproducible conditions. This is important because in accordance with the process according to the invention described above, a calibration of the measurement chamber is performed first, for which it is advantageous to use mathematical models that in turn require calculable geometric conditions in the measurement chamber.

In a preferred development of the device according to the invention, the measurement chamber is lined with a radioactive material. This feature has the advantage, known in the art, that if a suitable radioactive material is selected, for example $Ni^{63}$ with an activity of 10 mCi, a sufficiently inhomogeneous distribution of reaction ions and thus of quasi-molecular ions occurs in a cylindrical measurement volume 10 mm in diameter and between 10 and 30 mm long.

It is furthermore preferable if the walls of the measurement chamber are made of a plastic, since this makes them especially easy to produce.

It is furthermore preferable if the electrode pair consists of an axial rod electrode and an electrically conductive lining of the cylindrical enveloping surface of the measurement chamber.

This feature has the advantage of resulting in an electrode arrangement that is easy to manage in terms of calculation. The feature has the additional advantage that the radioactive lining of the measurement chamber can simultaneously be used as the outer electrode.

Lastly, it is preferred if the rod electrode has a stainless-steel surface. This has the advantage of making available an element for the rod electrode that is electrically conductive but not chemically active.

Altogether, the invention thus has the advantage of allowing very rapid detection of measured substances; for example, the aforesaid vesicants or nerve poisons can be detected with a measurement time of about 10 seconds, within a typical concentration range of 10 to 100 ppb.

The possibility of calibrating the measurement chamber on the basis of mathematical models also has the advantage of allowing optimization for certain measured substances essentially without practical tests, eliminating the need for hazardous and therefore complex laboratory experiments with measurement chambers of different designs.

The invention can therefore advantageously be used in the entire area of environmental engineering and military engineering. It is described hereinafter, however, with reference to the example of detecting gaseous warfare agents, although this application in no way limits the invention.

It also goes without saying that the features mentioned previously and those yet to be explained below can be used not only in the particular combinations indicated, but also in other combinations or in isolation, without leaving the context of the present invention.

BRIEF DESCRIPTION OF THE DRAWING

Exemplary embodiments of the invention are depicted in the drawings and will be explained in more detail in the description below. In the drawings.

DESCRIPTION OF THE PREFERRED EMBODIMENTS

Figure 1:
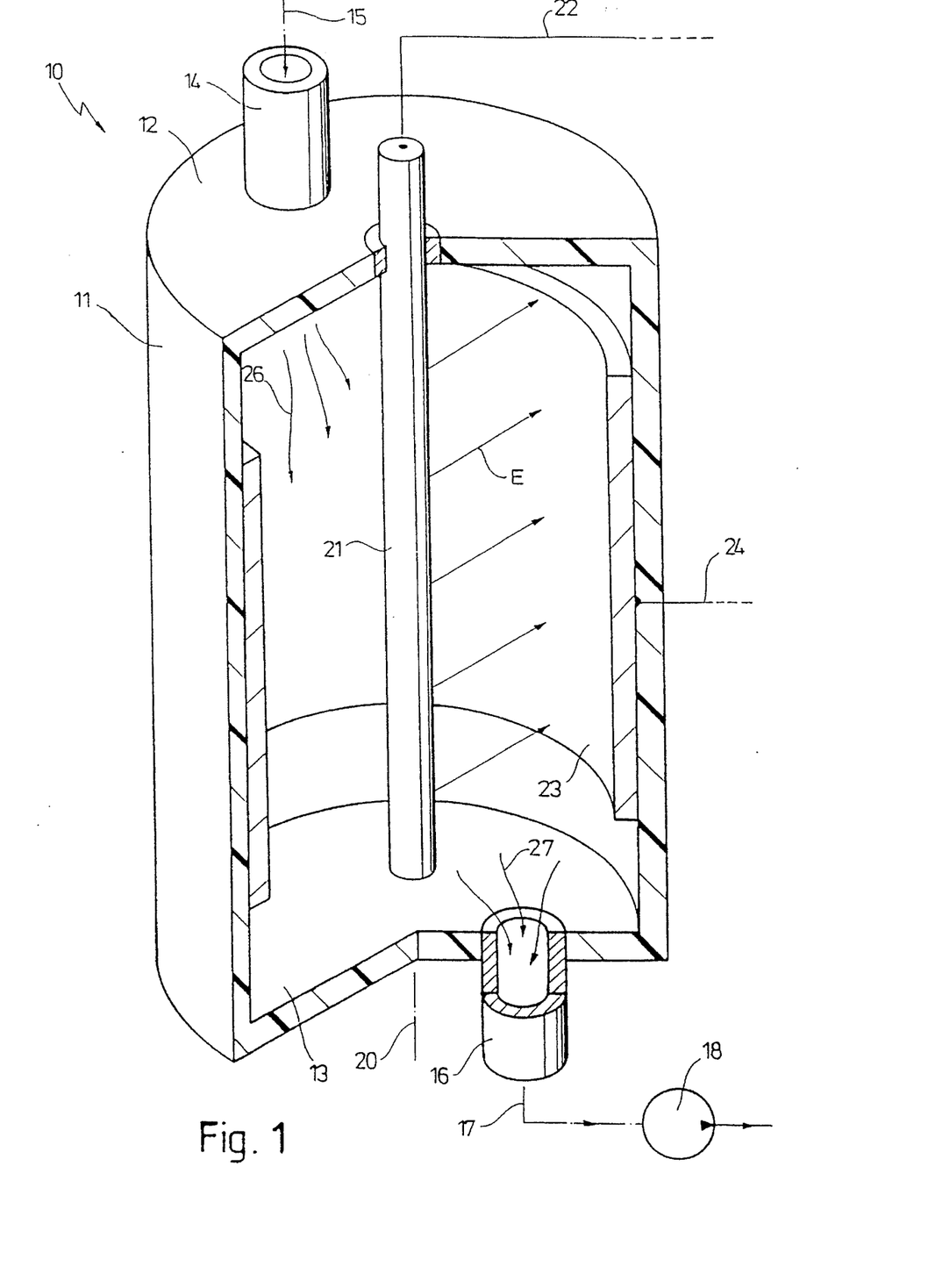
FIG. 1 is a perspective view, partly cut away, through a measurement chamber as used in the context of the present invention.

In FIG. 1, 10 designates a cylindrical measurement chamber that is essentially defined by a cylindrical casing 11, an upper end wall 12, and a lower end wall 13. In this respect the measurement chamber 10 is preferably made of a plastic, for example polyethylene or polypropylene, and can be produced as an injection-molded housing.

Located in the upper end wall 12 is an inlet tube 14 through which, as indicated by an arrow 15, a medium, for example ambient air, can be drawn in.

Located correspondingly in the lower end wall 13 is an outlet tube 16 which is connected to a conduit 17. The conduit 17 leads to a suction pump 18. The end walls 12, 13 are made of insulating material, preferably polyethylene or polypropylene.

Arranged along one axis 20 of the measurement chamber 10 is a rod electrode 21 that extends through the upper end wall 12 and is preferably spaced a certain distance away from the lower end wall 13. The rod electrode 21 preferably consists, at least on its surface, of a chemically inactive material, for example stainless steel. The rod electrode 21 is connected to a first lead 22 that will be further explained later on.

Located on the inside of the cylindrical casing 11 is a lining 23 made of a radioactive material. The lining 23 preferably consists of a radioactive nickel isotope, specifically $Ni^{63}$. Since the lining 23 is electrically conductive, it can simultaneously serve as the outer electrode, i.e. as the electrode that cylindrically surrounds the rod electrode 21 which acts as the inner electrode. For this purpose, the lining 23 is connected to a second lead 24 that is guided through the cylindrical casing 11 and whose function will be further explained in detail later on.

In one practical exemplary embodiment of the measurement chamber 10, the latter has an inside diameter of 10 mm and an axial length of 10 to 30 mm. For measurements of gaseous substances, the suction pump 18 is set for a gas flow rate of 10 to 30 liters/hour. The gas then flows through the inlet tube 14 into the measurement chamber 10, as indicated by arrows 26, and is extracted from the measurement chamber 10 through the outlet tube 16, as indicated by arrows 27.

With the geometry of the measurement chamber 10 as described above, the lining 23 has, for example, an activity of 10 mCi.

A radially oriented electric field, indicated in FIG. 1 by arrows labeled E, forms when a voltage is applied via the leads 22, 24 to the electrodes 21, 23.

FIG. 2 once again shows the measurement chamber 10 on the left side, in a highly schematic sectioned view.

Figure 2:
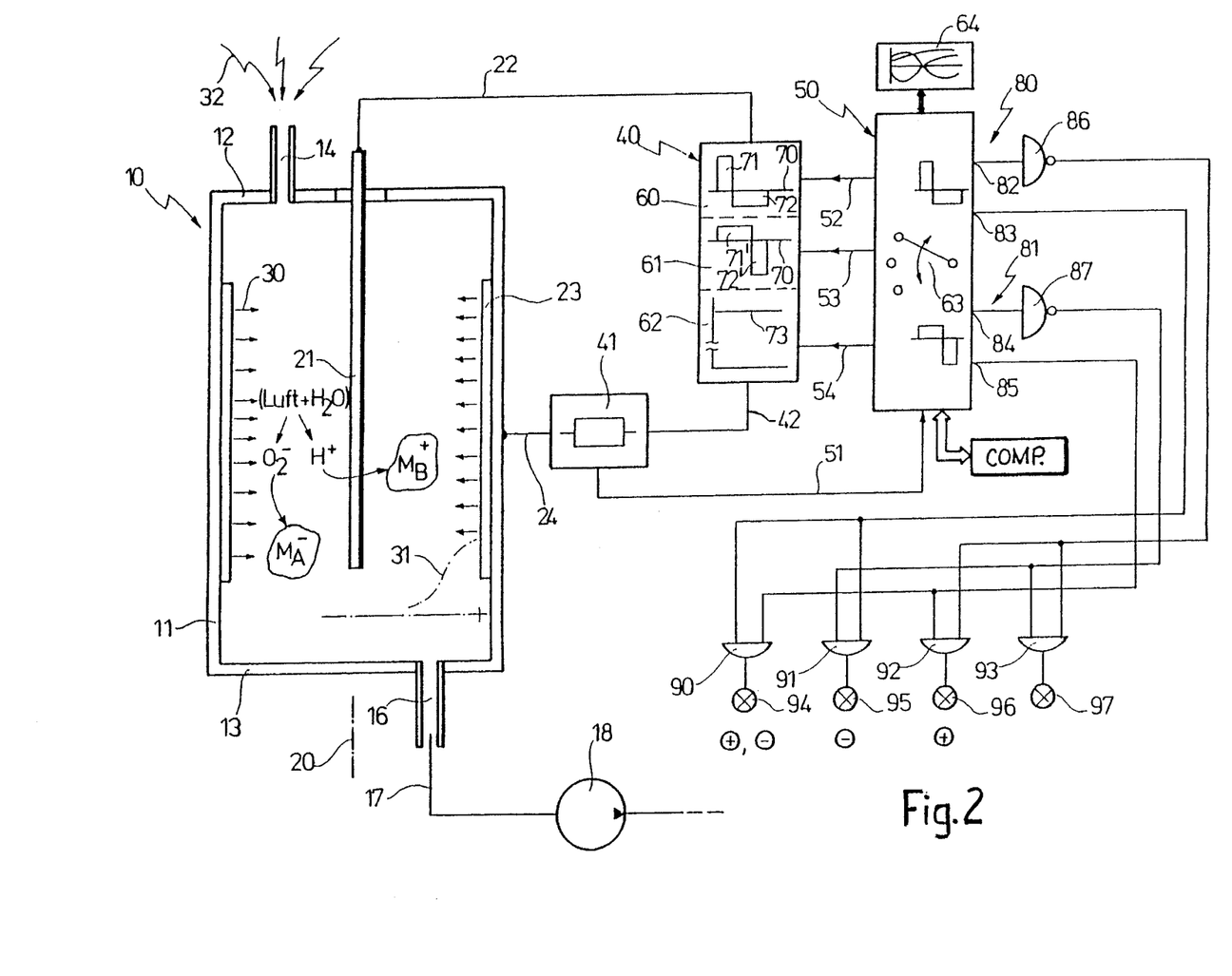
FIG. 2 is a highly schematic block circuit diagram explaining one exemplary embodiment of a device according to the invention.

FIG. 2 also indicates the β radiation emerging from the radioactive lining 23 at 30. Indicated at 31 with dot-dash lines is a radial plot of the intensity of the β radiation 30, showing that the β radiation 30 has already decayed sharply after a few millimeters, and in any event over a distance that is considerably less than the radius of the measurement chamber 10.

As a result, an inhomogeneous distribution of radiation intensity is created in a radial plane of the measurement chamber 10, since the intensity rapidly decreases from the inner periphery of the measurement chamber 10, i.e. from the radioactive lining 23, inwards towards the axis 20.

If a gas mixture, indicated in FIG. 2 as 32, is then drawn into the measurement chamber 10 through the inlet tube 14, the following occurs (if the gas mixture 32 is of suitable composition ):

Let it be assumed that the gas mixture 32 consists essentially of ambient air which nevertheless contains certain fractions of two measured substances A and B. These measured substances A and B may be, for example, gaseous warfare agents, and in particular, measured substance A may be a vesicant and measured substance B may be a nerve poison.

The moisture (water) present in the ambient air is now exposed to the β radiation 30 in the measurement chamber 10. The β radiation 30 has an ionizing effect, resulting in the formation, from the atmospheric moisture which is used as the reaction substance, of reaction ions, namely negatively charged oxygen ions ($O_2-$) on the one hand and positively charged protons ($H^+$) on the other hand, as depicted schematically in FIG. 2.

Let is further be assumed that the molecules $M_A$ of the first measured substance (gaseous vesicants) have an affinity for the negatively charged oxygen ions ($O_2-$), whereas the molecules $M_B$ of the second measured substance (gaseous nerve poisons) have an affinity for the positively charged reaction ions ($H^+$). The corresponding reaction ions therefore attach themselves to the respective molecules, resulting in electrically charged quasi-molecular ions $M_A-$ and $M_B+$.

It must be noted in this connection that the number of reaction ions generated by ionization is very much greater than the number of measured substance ions present in the ambient substance, so that even after attachment to the reaction ions, there is still a great excess of unattached reaction ions.

Also worth noting is that the weight of the reaction ions is considerably less, specifically about two to five times less, than the molecular weight of the measured substance ions.

Once ionization and attachment have occurred, the measurement chamber 10 thus contains high-mobility reaction ions $O_2-$ and $H^+$, and low-mobility quasi-molecular ions $M_A-$ and $M_B+$. The concentrations of these various charge carriers are, however, initially unknown.

A three-channel voltage source 40 is then used to generate the electric field E inside the measurement chamber 10. The voltage source 40 is connected, in series with a measurement resistor 41 and a third conductor 42, to the leads 22 and 24 mentioned earlier, resulting altogether in a closed circuit. Specifically, when the voltage source 40 applies a voltage to the electrodes 21, 23, the charge carriers located in the measurement chamber are thereby set in motion, and an ion current—detectable at the measurement resistor 41 as a voltage drop—flows.

A control unit 50, that is connected via a measurement conductor 51 to the measurement resistor 41 and via three control conductors 52, 53, 54 to the three channels of the voltage source 40, is provided in order to control the measurement process.

The first channel 60 of the voltage source 40 is a first pulse generator, the second channel 61 is a second pulse generator, and the third channel 62 is a constant voltage generator.

A selector switch labeled 63 in the control unit 50 can now be used to switch the first, second, or third channel 60, 61, or 62 alternatively into the circuit.

It is self-evident in this connection that the circuit elements already described, as well as the circuit elements yet to be explained below, can in each case be configured as separate electrical components (hardware), or as software in the context of a control program.

Lastly, the control unit 50 is also connected to a characteristic curve memory 64, which will be explained in further detail below.

Time-varying voltage profiles, preferably having the shape of periodic pulse sequences, are generated in the channels 60 and 61 of the voltage source 40 that are configured as pulse generators. For example, as indicated in FIG. 2, a pulse sequence can alternate about a zero line 70, with a first pulse 71 being a positive, narrow, high pulse, while a second pulse 72 is a negative, broad, flat pulse. Preferably the total pulse areas of the pulses 71 and 72 are equal in magnitude.

A similar pulse sequence 71', 72' with reference to the zero line 70, in which the shape and polarity of the pulses are simply transposed with respect to the pulses 71, 72, is generated in the second channel 61.

In the pulses 71, 72 and 71', 72' the ratio between height and width is preferably between two and five.

Lastly, a constant voltage 73, the magnitude of which is several times greater than the effective value of the pulse sequences 71, 72 or 71', 72', is generated in the third channel 62. Preferably the amplitude of the constant voltage 73 is two to twenty times the effective value of the pulse sequences, so when the constant voltage 73 is applied to the electrodes 21, 23, an electric field strength of, for example, 1000 V/cm is generated in the measurement chamber 10.

A first measurement output 80 for measurements with the first channel 60 and a second measurement output 81 for results of measurements with the second channel 61 are provided on the control unit 50. Since each measurement output 80, 81 has two connections, a total of four connections 82 to 85 are available. Two of these connections 82, 84 are inverted with inverters 86, 87. The four output conductors that result are directed, in the manner illustrated in FIG. 2, to four AND gates 90 to 93, with indicators 94 to 97 connected downstream from each of them.

The indicator 94 indicates the simultaneous presence of nerve poisons (+) and vesicants (−); the second indicator 95 indicates that only vesicants (−) were detected; the third indicator 96 indicates the presence of nerve poisons (+) only; while the fourth indicator signals that neither vesicants nor nerve poisons were detected.

Figure 3:
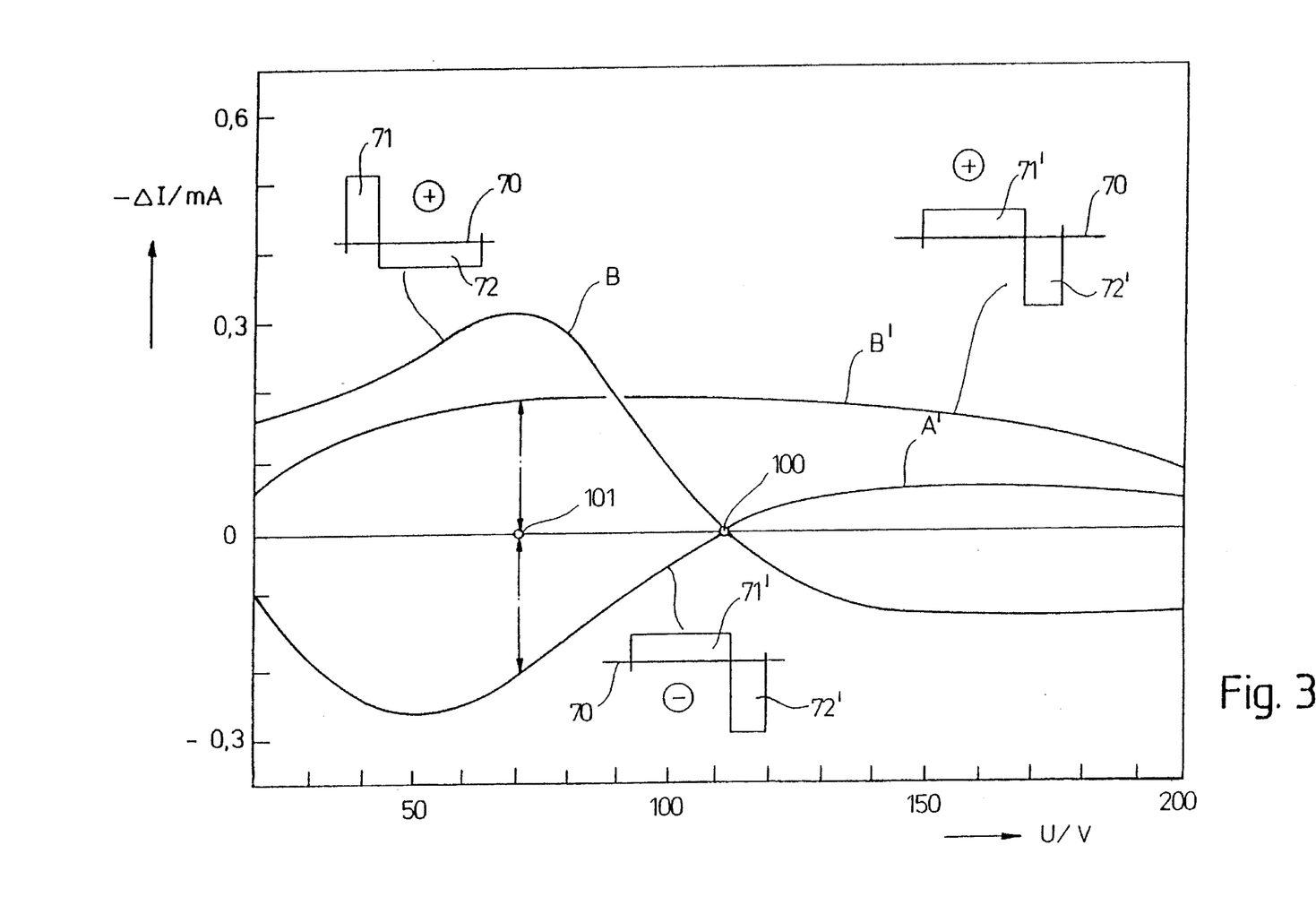
FIG. 3 is a calibration diagram explaining one exemplary embodiment of the process according to the invention.

To explain the operation of the arrangement according to FIG. 2, first of all the family of characteristic curves in FIG. 3 will be described:

FIG. 3 is a plot of calibration curves that were determined using mathematical models for a defined geometry of a measurement chamber 10 under defined boundary conditions. In the characteristic curves in FIG. 3, the quasi-molecular ion current $\Delta I$ is plotted on the ordinate, while the effective value of the voltage applied to the electrodes 21, 23 is plotted on the abscissa.

A first characteristic curve in FIG. 3 is labeled B. Curve B applies to a predetermined existing concentration of measured substance B (nerve poisons). Curve B indicates the quasi-molecular ion current of quasi-molecular ions $M_B+$ when the first channel 60 of the voltage source 40 was switched to the measurement chamber 10, i.e. when a voltage profile with the pulses 71, 72 was in effect. It is evident that the molecular ions $M_B+$ of the first measured substance B initially result, at low effective voltages U, in only a small molecular ion current $\Delta I$, which then rises to a maximum, drops to zero as the effective voltage increases further, and then decreases to a negative limit value.

Similarly, curve B' in FIG. 3 shows the change in molecular ion current under the same conditions, the only difference being that this time the second channel 61 of the voltage source 40 was switched on. Under these conditions, the curve for the molecular ion current $\Delta I$ as a function of effective voltage U is different: specifically, the molecular ion current $\Delta I$ remains constant, with a weakly developed maximum.

Lastly, A' depicts a third curve which plots the correlation between the molecular ion current $\Delta I$ for the molecular ions $M_A-$ of the first measured substance A (vesicants) as a function of the effective voltage U. The shape of curve A' is similar to that of curve B, although of opposite sign. It is interesting that curves B and A' intersect approximately at the zero point 100.

Curves B, B', and A'—which, as mentioned, were determined by theoretical or practical preliminary tests—are stored in the characteristic curve memory 64 in the device in FIG. 2, and influence the operation of the control unit 50.

At this point it is worth mentioning again that the diagram in FIG. 3 refers only to a specific configuration of the measurement chamber 10, namely to a predefined geometry and to predefined measurement parameters, for example including a predefined frequency for the pulses 71, 72 and 71', 72'. It goes without saying in this connection that a large number of characteristic curve families like those in FIG. 3 can be determined for various measurement chambers or measurement conditions, and stored in each case in the characteristic curve memory 64 for various practical measurements.

We will now assume that all the measurement parameters that, for example, served as the basis for the diagram in FIG. 3, have been applied in the arrangement in FIG. 2.

The effective voltage of the pulses 71, 72 and 71', 72' can now be freely selected within the range of variation of the diagram in FIG. 3. It is advantageous if a measurement is performed at the zero point 100, i.e. if, in the case of the example depicted in FIG. 3, the pulses 71, 72 or 71', 72' are set so that the effective voltage is on the order of 110 V.

If the first channel 60 of the voltage source 40 is then switched into the circuit of the measurement chamber 10 by actuating the selector switch 63, any molecular ion current $\Delta I$ will then generate a voltage at the measurement resistor 41 which will be transferred via the measurement conductor 51 to the control unit 50.

If no measured signal is observed during this test, this means that no $M_A-$ molecular ions are present (since at this operating point they would have resulted in a molecular ion current); but the result does not also mean that no $M_B+$ molecular ions are present, since the intersection of curve B with the zero point 100 indicates that even if $M_B+$ molecular ions were present, no quasi-molecular ion current $\Delta I$ would be generated.

If, however, a measured signal occurs during the measurement, this means that $M_A-$ quasi-molecular ions must be present, but once again no statement can be made concerning the presence of $M_B+$ quasi-molecular ions, since at the zero point 100, a quasi-molecular ion current can never result from $M_B-$ quasi-molecular ions.

With this intermediate result in hand, the system is switched to the second channel 61, and a measurement with the pulses 71', 72' is immediately performed. The measurement point is once again the zero point 100.

If once again no measured signal occurs with this second measurement, this means (when considered in isolation) that no $M_B+$ quasi-molecular ions can be present, since, on the evidence of curve B' in FIG. 3, they would necessarily have produced a molecular ion current at an effective voltage of 110 V.

On the other hand, the absence of the measured signal in this isolated case does not also mean that no $M_A-$ molecular ions are present, since here again it is fundamentally impossible for any measured signal from $M_A-$ quasi-molecular ions to be generated at the zero point 100.

If, on the other hand, the second measurement yields a positive measured signal, this means that $M_B+$ quasi-molecular ions at least are present, while on the other hand it is once again impossible to make any statement concerning $M_A-$ quasi-molecular ions.

These four possible results must then be fed out to the outputs 82 to 85 of the control unit 50. In the case of the first measurement with the first channel 60, the zero signal (no measured current) is present at the output 82, while a positive measured signal (measured current present) would exist at output 83. The same applies for outputs 84 and 85 for measurements with the second channel 61.

The four possible output signals from the two measurements are then correlated by means of the logical elements 86, 87, and 90 to 93 so as to display the four possible results.

For example, if neither $M_A-$ quasi-molecular ions nor $M_B+$ quasi-molecular ions are present, no measured signal will occur on either channel 60 or 61 during the two measurements. In the depiction in FIG. 2, this zero signal is present at the outputs 82 and 84, is reshaped in the inverters 86, 87 into positive signals, and in that form passes to the two inputs of the AND gate 93, thus illuminating the indicator 97 which indicates that neither of the two measured substances A or B was present in the gas mixture 32.

If, on the other hand, both measured substances A and B were present in the gas mixture 32, a positive measured signal will then be generated in both measurements, and will thus be applied as positive logical signals to the outputs 83 and 85. The AND gate 90 will consequently become conductive and actuate the associated indicator 94. The same applies for the two additional indicators for isolated occurrence of the first measured substance A (indicator 95) or measured substance B (indicator 96).

It goes without saying in this context that the logic depicted in FIG. 2 was made relatively complex in configuration solely for purposes of clarity, and that in an actual application, other logical elements and connections can also be used.

It also goes without saying that the measurements do not necessarily need to be performed at the zero point 100. Other measurement points can also be selected, provided no undesired compensation occurs because calibration curve values have the same magnitude but different signs. One such "forbidden" operating point is labeled 101 in FIG. 3.

In a third step, or in a step preceding the first step, the third channel 62 of the voltage source 40 can now be switched in, thus applying the very high constant voltage 73 to the electrodes 21, 23.

The result of applying the very high constant voltage 73 with a very high static electric field strength of, for example, 1000 V/cm, is that all the charge carriers located in the measurement chamber 10, i.e. the mobile reaction ions $O_2-$ and $H^+$ as well as the relatively slow-moving quasi-molecular ions $M_A-$ and $M_B+$, migrate to the respective electrode, thus producing a total ion current that corresponds to the total number of free charge carriers in the measurement chamber 10.

This measurement result, in connection with the two previous measurements using channels 60 and 61, now makes it possible first to undertake quantitative measurements and thus determine concentrations of the measured substances A and B, while on the other hand concentrations of interfering substances can also be determined and thus subtracted; lastly, the effect of external interfering influences, for example due to fluctuations in temperature, pressure, and humidity, also becomes evident.

The last statement is true because the three measurements with channels 60, 61, and 62 are performed in immediate succession, for example at intervals of 100 ms, so that all three measurements are performed under the same conditions (which may be affected by interference), and these interfering variables become evident by comparing the measurements.

With regard to determining the concentration of the measured substances A and B and any interfering substances that may be present, it must be remembered that in the first two measurements with channels 60 and 61, the result in each case is a function of the (known) attachment probability, the (unknown) concentration of the molecules of measured substances A and B, the (unknown) concentration of the molecules of the interfering substance, and the (also unknown) concentration of the reaction ions.

But if the total number of charge carriers was determined by means of the third (or prior) measurement, and if on the other hand the ratio between the concentrations of the molecules of the measured substances is known because a ratio has been defined between the first and the second measurement, the remaining unknown variables can thus be determined by calculation or by suitable calculation circuitry as might be included in a suitable computational unit 89.

A calculation of this kind can, for example, be performed as follows:

First the equations for product ion formation are considered, as follows:

in which $H_2O$ is the contribution of water clusters to the reaction ions due to atmospheric humidity of the ambient air; $H^+$ and $O_2-$ designate the reaction ions; and A and B in turn indicate the measured substance to which the positive reaction ions $H^+$ or negative reaction ions $O_2-$ are respectively attached. In the example explained above, A thus again designates the group of nerve poisons, and B the group of vesicants.

X and Y denote the probabilities of formation applicable to the ionization of measured substances A and B respectively. The formation probabilities X, Y could be defined by ion mobility spectroscopy (IMS) if ideal conditions are present, although this requires expensive and complex apparatus.

If we now consider the three different measurements of the types described in detail above, namely the zero-point measurement at high voltage as well as the two pulse measurements, the formation probabilities X and Y are reduced by different amounts in each of the three measurements. This is indicated hereinafter by the indices $X_1$, $X_2$, $X_3$ and $Y_1$, $Y_2$, and $Y_3$. The respective reduction factors $X_1/X$, $X_2/X$, $X_3/X$ and $Y_1/Y$, $Y_2/Y$, $Y_3/Y$ can be defined, according to the invention, by ion mobility spectroscopy in which the ion source is also the measurement cell of the device.

Furthermore, a constant K is used hereinafter to denote the number of unattached residual ions, with K being dependent on the pressure, temperature, drift velocity, half-life, and the like, in other words the general measurement conditions.

If we then initially consider, as the first measurement, the zero-point measurement at high voltage, we find the following for the resulting ion current $I_1$:

$$I_1 = K + X_1 A + Y_1 B$$

If we then consider that in this case $X_1$ and $Y_1$ are approximately zero, since the reaction ions have a very high velocity compared to the quasi-molecular ions, we get approximately the following result for the ion current in this measurement:

$$I_1 \approx K$$

If we then consider the second case—ionization of the first measured substance A—we get for the resulting ion current $I_2$:

$$I_2 = K + X_2 A + Y_2 B$$

with the additional fact that in this case $X_2$ is much greater than $Y_2$.

For the third measurement instance—ionization of measured substance B—we get the following for the resulting ion current $I_3$:

$$I_3 = K + X_3 A + Y_3 B$$

with $X_3$ being much smaller than $Y_3$ in this case.

From these three measurement results, we can thus define the concentration of measured substance A as $$A = (I_2 - I_1 - Y_2 A)/X_2 = (I_3 - I_1 - Y_3 B)/X_3$$

and the concentration of measured substance B as $$B = \left( \frac{X_2}{X_3} (I_3 - I_1) - (I_2 - I_1) \right) / \left( \frac{X_2}{X_3} Y_3 - Y_2 \right).$$

We claim:

1. A method of detecting a gaseous warfare agent in the presence of an interfering compound in ambient air, comprising the steps of:

providing a measuring chamber having spaced apart electrodes for generating therein an electrical field, at least one of said electrodes containing radioactive material and the separation between said electrodes being substantially greater than the half-life range of the radioactive material, said electrical field being developed by applying selected voltages across said electrodes;

developing a first plurality of characteristic curve data by plotting the quasi-molecular ion current flowing from one of said electrodes to the other versus the applied voltage when first and second asymmetric time varying voltages are alternately selected and applied across said electrodes and various known concentrations of said gaseous warfare agent are caused to flow through said measuring chamber;

developing a second plurality of characteristic curve data by plotting the quasi-molecular ion current flowing from one of said electrodes to the other versus the applied voltage when first and second asymmetric time varying voltages are alternately selected and applied across said electrodes and various known concentrations of said interfering compound are caused to flow through said measuring chamber;

causing a sample of ambient air including a reactive compound and believed to include at least one of said gaseous warfare agent and said second interfering compound to flow through said chamber and in said electric field, the radiation from said radioactive material having an ionizing effect on said reactive compound thereby generating negatively charged ions and positively charged ions that will attach to molecules of said gaseous warfare agent and said interfering compound present in said sample thereby forming electrically charged quasi-molecular ions;

applying said asymmetric first time varying voltage across said electrodes;

measuring any resulting first quasi-molecular ion current flowing from one of said electrodes to the other;

comparing the measured first quasi-molecular ion current to each of said first plurality of characteristic curves and developing a first detection signal indicating whether or not a match to one of said first characteristic curves is detected;

comparing the measured first quasi-molecular ion current to each of said second plurality of said characteristic curves and developing a second detection signal indicating whether or not a match to one of said second characteristic curves is detected;

applying said asymmetric second time varying voltage across said electrodes;

measuring any resulting second quasi-molecular ion current flowing from one of said electrodes to the other;

comparing the measured second quasi-molecular ion current to each of said first plurality of characteristic curves and developing a third detection signal indicating whether or not a match to one of said first characteristic curves is detected;

comparing the measured second quasi-molecular ion current to each of said second plurality of characteristic curves and developing a fourth detection signal indicating whether or not a match to one of said second characteristic curves is detected; and logically combining said first, second, third and fourth detection signals to generate an output signal indicative of the presence of at least one of said gaseous warfare agent and said interfering compound, or the lack thereof, in said sample of ambient air.

2. A method as recited in claim 1 wherein water is used as said reaction compound.

3. A method as recited in claim 1 wherein said reactive material is a β-radiator, and wherein the radiation emerging from said one electrode has a particular intensity decay profile, and wherein the spatial separation between said electrodes is substantially greater than the half-maximum intensity point of said decay profile.

4. A method as recited in claim 1 wherein said first and second time varying voltages have basic frequencies in the range between 100 Hz and 500 Hz.

5. A method as recited in claim 1 wherein said measuring chamber has a volume in the range of between 0.5 cm$^3$ and 5 cm$^3$.

6. A method as recited in claim 1 and further comprising the steps of:

applying a predetermined constant voltage across said electrodes to generate a constant electrical field therebetween having a field strength two to twenty times higher than the mean field strength of the fields generated in said measuring chamber by the application of said first and second time varying voltages, measuring the resulting third quasi-molecular ion current to provide a fifth detection signal, and using said fifth detection signal in conjunction with said first, second, third and fourth detection signals to determine the concentrations of the measured gaseous warfare agent and/or interfering compound in the sample.

7. A method as recited in claim 6 wherein said constant electrical field has a field strength of approximately 100 volts per centimeter.

8. A method as recited in claim 1 wherein said first time varying voltage has a waveform including first and second pulses of alternating polarity.

9. A method as recited in claim 8 wherein each said first pulse is followed immediately by one of said second pulses.

10. A method as recited in claim 8 wherein said first pulses have the same pulse area as said second pulses.

11. A method as recited in claim 8 wherein said second time varying voltage has a waveform including third and fourth pulses of alternating polarity, the respective polarities of said third and fourth pulses being opposite to the polarities of said first and second pulses.

12. A method as recited in claim 8 wherein said first and second time varying voltages have mean values in the range of between 50 volts and 200 volts.

13. A method as recited in claim 8 wherein said pulses are of rectangular shape with said first pulse being greater in amplitude and narrower in time than said second pulse.

14. A method as recited in claim 13 wherein the amplitude of said first pulse is 2 to 5 times as high as that of said second pulse.

15. Apparatus for detecting a predetermined gaseous warfare agent in the presence of a predetermined interfering compound in a sample of ambient air, comprising:

means providing a measuring chamber having spaced apart electrodes disposed therein, at least one of said electrodes having radioactive material forming a part thereof, an inlet port and an outlet port;

three channel voltage supply means for selectively applying predetermined asymmetric first and second time varying voltages across said electrodes to develop an electrical field therebetween;

means for detecting quasi-molecular ion current flowing from one of said electrodes to another through a sample of ambient air contained in said chamber;

memory means having a series of characteristic curve data stored therein, a first group of said curve data corresponding to quasi-molecular ion currents previously detected as said first and second time varying voltages was alternately applied across said electrodes, and various known concentrations of said gaseous warfare agent were caused to flow through said chamber, and a second group of said curve data corresponding to quasi-molecular ion currents previously detected as said first and second time varying voltages was applied across said electrodes, and various known concentrations of said interfering compound were caused to flow through said chamber;

means for comparing detected quasi-molecular ion currents to said series of characteristic curve data to develop first, second, third and fourth detection signals as a sample of ambient air is caused to flow through said chamber, said first detection signal being indicative of a match, or lack thereof, between a detected quasi-molecular ion current and one of said first group of curve data when said asymmetric first time varying voltage is applied across said electrodes, said second detection signal being indicative of a match, or lack thereof, between a detected quasi-molecular ion current and one of said second group of curve data when said asymmetric first time varying voltage is applied across said electrodes, said third detection signal being indicative of a match, or lack thereof, between a detected quasi-molecular ion current and one of said first group of curve data when said asymmetric second time varying voltage is applied across said electrodes, and said fourth detection signal being indicative of a match, or lack thereof, between a detected quasi-molecular ion current and one of said second group of curve data when said asymmetric second time varying voltage is applied across said electrodes; and logic means responsive to said first, second, third and fourth detection signals and operative to generate an output signal indicative of the presence of at least one of said gaseous warfare agent and said interfering compound, or the lack thereof, in said sample of ambient air.

16. Apparatus as recited in claim 15 wherein said measuring chamber is cylindrical in configuration.

17. Apparatus as recited in claim 15 wherein said one electrode having radioactive material defines an outer boundary of said measuring chamber.

18. Apparatus as recited in claim 15 wherein walls of said measuring chamber are made of a plastic material.

19. Apparatus as recited in claim 15 wherein one of said electrodes is in the form of an elongated rod extending into said measuring chamber, and a second electrode is an electrically conductive lining on an interior surface of a container forming said measuring chamber.

20. Apparatus as recited in claim 19 wherein said rod electrode has a stainless steel surface.

21. Apparatus as recited in claim 15 wherein said voltage supply means can also selectively apply a constant voltage across said electrodes to generate a constant electrical field therebetween, whereby a resulting quasi-molecular ion current can be detected and used in conjunction with said first, second, third and fourth detection signals to determine the concentrations of the measured gaseous warfare agent and/or interfering compound in the sample.

22. Apparatus as recited in claim 21 and further comprising computational means associated with said comparing means for using the detected value of said resulting quasi-molecular ion current in conjunction with said first, second, third and fourth detection signals to calculate the concentrations of the measured gaseous warfare agent and/or interfering compound in the sample.

* * * * *

UNITED STATES PATENT AND TRADEMARK OFFICE
CERTIFICATE OF CORRECTION

PATENT NO. : 5,510,268
DATED : April 23, 1996
INVENTOR(S) : Doring, et. al.

It is certified that error appears in the above-indentified patent and that said Letters Patent is hereby corrected as shown below:

Title page, after item [76] inventors and before item [21] Appl. No.: 308,947 insert-- the following:

Item [73] Assignee: should read--Bruker-Saxonia Analytik GmbH Leipzig, Federal republic of Germany--.

Signed and Sealed this

Eleventh Day of February, 1997

Attest:

BRUCE LEHMAN

*Attesting Officer*  *Commissioner of Patents and Trademarks*